United States Patent
Allmendinger et al.

(10) Patent No.: US 10,013,759 B2
(45) Date of Patent: Jul. 3, 2018

(54) METHOD AND IMAGE DATA PROCESSING DEVICE FOR PROCESSING A MULTI-ENERGY COMPUTERIZED TOMOGRAPHY IMAGE DATA SET

(71) Applicant: Siemens Healthcare GmbH, Erlangen (DE)

(72) Inventors: Thomas Allmendinger, Forchheim (DE); Thomas Flohr, Uehlfeld (DE); Bernhard Krauss, Burgthann (DE); Bernhard Schmidt, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 22 days.

(21) Appl. No.: 15/359,709

(22) Filed: Nov. 23, 2016

(65) Prior Publication Data

US 2017/0301082 A1    Oct. 19, 2017

(30) Foreign Application Priority Data

Nov. 27, 2015    (DE) .......................... 10 2015 223 606

(51) Int. Cl.
*G06K 9/00*    (2006.01)
*G06T 7/00*    (2017.01)

(52) U.S. Cl.
CPC .. *G06T 7/0012* (2013.01); *G06T 2207/10081* (2013.01); *G06T 2207/30008* (2013.01)

(58) Field of Classification Search
CPC ......... G06T 7/0012; G06T 2207/10081; G06T 2207/30008
See application file for complete search history.

(56) References Cited

U.S. PATENT DOCUMENTS

| | | | |
|---|---|---|---|
| 2007/0217570 | A1 | 9/2007 | Grasruck et al. |
| 2011/0142322 | A1* | 6/2011 | Kabus .................. G06T 3/0075 382/131 |
| 2013/0083989 | A1 | 4/2013 | Flohr et al. |
| 2013/0317369 | A1* | 11/2013 | Bryant-Greenwood A61B 5/0059 600/476 |

FOREIGN PATENT DOCUMENTS

| | | |
|---|---|---|
| DE | 102006009222 A1 | 9/2007 |
| DE | 102011083727 A1 | 4/2013 |

* cited by examiner

*Primary Examiner* — Shefali Goradia
(74) *Attorney, Agent, or Firm* — Harness, Dickey & Pierce, P.L.C.

(57) ABSTRACT

A method is for processing a first image data set including a first image value tuple associated with a volume element of a region of an object to be imaged. In an embodiment, a second image data set is generated based upon the first image data set, including a second image value tuple associated with the volume element, a base material decomposition being capable of being carried based upon the second image data set and based upon a base material set; a starting area and a target area are selected as a function of the base material set, the first image value tuple being located in the starting area; the second image value tuple is ascertained based upon the first image value tuple, the second image value tuple being associated with the first image value tuple via image value tuple imaging and being located in the target area.

30 Claims, 4 Drawing Sheets

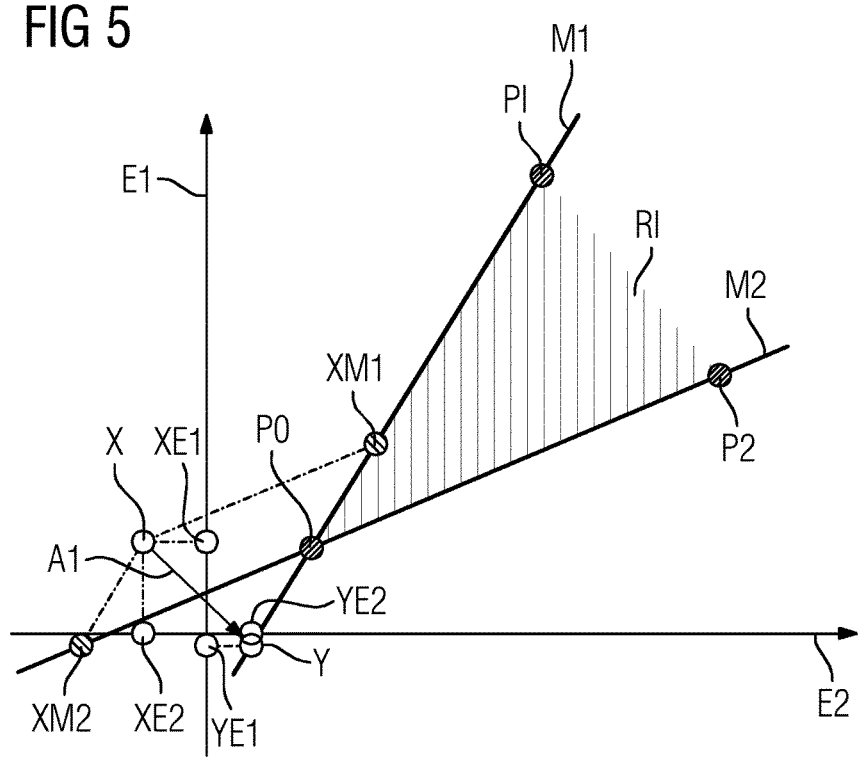
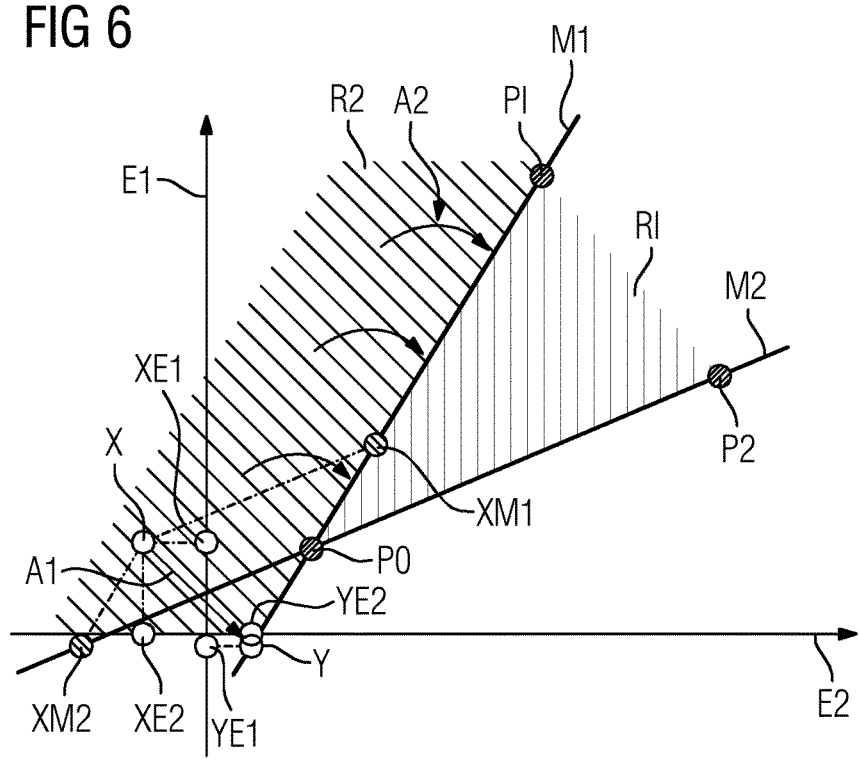

METHOD AND IMAGE DATA PROCESSING DEVICE FOR PROCESSING A MULTI-ENERGY COMPUTERIZED TOMOGRAPHY IMAGE DATA SET

PRIORITY STATEMENT

The present application hereby claims priority under 35 U.S.C. § 119 to German patent application number DE 102015223606.4 filed Nov. 27, 2015, the entire contents of which are hereby incorporated herein by reference.

FIELD

At least one embodiment of the invention generally relates to a method for processing a first image data set, wherein a second image data set is generated on the basis of the first image data set, wherein a base material decomposition can be carried out on the basis of the second image data set and on the basis of a base material set. At least one embodiment of the invention also generally relates to an image data processing device, to an imaging device, to a computer program product and to a computer-readable medium.

BACKGROUND

Base material decomposition is a generally known method for analyzing image data sets that have been generated with multi-spectral computerized tomography (CT) imaging, in particular have been recorded with a dual-energy CT scan. The method of base material decomposition has been described by Alvarez and Macovski in [AM76]. Base material decomposition can be performed, in particular, in the raw data space (projection-based) or in the image space (image-based).

DE 10 2006 009 222 A1 discloses a method and a device for determining the concentration of a substance in a body material by way of multi-energy computerized tomography.

With base material decomposition CT images can be calculated in which the base materials are selectively displayed. For example, with water/iodine decomposition, water is displayed fully in the water base material image and iodine fully in the iodine base material image. All other materials can be displayed partly in one image and partly in the other image.

The three-material decomposition known to a person skilled in the art represents an improvement in this traditional base material decomposition. The two base materials can be present in a shared surrounding material, such as, for example, soft tissue. The contrast agent image can then contain, for example, only iodine, while, for example, soft tissue and calcium or bones can be seen in the virtual non-contrast image.

An intensification of the image noise compared to the original images can occur in the result images with material decompositions of this kind. Noise reduction methods can be used to reduce this effect. Noise reduction is possible, for example, by using statistical information from the data of the image points adjacent to the image point, in particular neighboring voxels, for evaluation of an image point, in particular an image voxel. A noise reduction of this kind is a non-local operation therefore.

The image quality of the generally known base material decomposition can sometimes be affected by materials in the non-physical region of the decomposition if no additional correction is applied.

The physically expedient region of a base material decomposition may be taken to mean when the CT value of the second energy is plotted in a graph against the CT value of the first energy for a region in the dual-energy image, as is shown in FIG. 5. A wedge is obtained in the graph, and this corresponds to positive concentrations of the base material and therewith the physically expedient region of the base material decomposition. Further body materials can be located outside of the physically expedient region, however. When calculating base material images, these can be converted into positive and negative concentrations of the base materials. They can therefore be perceived to be disruptive.

This problem can occur in particular, with image-based three-material decomposition in blood, calcified atherosclerotic plaques and contrast medium. In this case the vascular calcification can be mathematically subtracted in order to see all other body materials and the contrast medium in the remaining image. An improved display of the vessel lumen can be achieved in this way. Negative calcium and positive iodine concentrations can, in particular, be associated with the image points relating to the fatty tissue and/or air, however. Therefore, fat and/or air on the one hand and contrast medium on the other cannot always be clearly distinguished. The presentation of vessels in the image can therefore be impaired after a calcium subtraction.

This problem can therefore occur, in particular, when materials are located outside of the physically permitted region of the base material in the case of image-based base material decomposition (with optional additional noise reduction).

A subsequent threshold value-based elimination of physically inexpediently decomposed materials cannot significantly improve the image quality in many cases since residual light edges occur due to partial volume effects and the finite range of image-based noise reduction filters.

DE 10 2011 083 727 A1 discloses a method for generating a noise-reduced CT image data set, a computing system and a CT system.

SUMMARY

At least one embodiment of the invention enables improved base material decomposition.

At least one embodiment is directed to a method, an image data processing device, an imaging device, a computer program product and a computer-readable medium.

At least one embodiment of the invention generally relates to a method for processing a first image data set which has been generated on the basis of multi-spectral computerized tomography imaging and which has a first image value tuple which is associated with a volume element of a region of an object to be imaged, wherein the method the comprises:

acquiring the first image data set,
processing the first image data set, and
supplying the second image data set.

Processing the first image data set, in at least one embodiment, comprises, in particular, the following steps:

wherein on the basis of the first image data set a second image data set is generated which has a second image value tuple associated with the volume element,
wherein a base material decomposition can be carried on the basis of the second image data set and on the basis of a base material set,
wherein a starting area and a target area are selected as a function of the base material set in the space of the image value, wherein the first image value tuple is located in the starting area, wherein the second image value tuple is ascertained on the basis of the first image value tuple, wherein the second image value tuple is associated with the first image value tuple via image value tuple mapping, and wherein the second image value tuple is located in the target area.

At least one embodiment of the invention also relates to an image data processing device for processing a first image data set, which has been generated on the basis of multi-spectral computerized tomography imaging and which has a first image value tuple which is associated with a volume element of a region of an object to be imaged.

In at least one embodiment, the image data processing device includes:

an acquisition module which is designed for acquiring the first image data set, a processing module which is designed for processing the first image data set, and a supply module, which is designed for supplying the second image data set.

In at least one embodiment, the processing module includes, in particular:

a generating module which is designed for generating a second image data set on the basis of the first image data set, wherein the second image data set has a second image value tuple associated with the volume element, wherein a base material decomposition can be carried out on the basis of the second image data set and on the basis of a base material set, a selection module which is designed for selecting a starting area and a target area dependent on the base material set, wherein the first image value tuple is located in the starting area and outside of the target area, an ascertaining module which is designed for ascertaining the second image value tuple on the basis of the first image value tuple, wherein the second image value tuple is associated with the first image value tuple via image value tuple mapping, wherein the second image value tuple is located in the target area.

In at least one embodiment, the invention also relates to a computer program product, comprising a computer program, wherein the computer program can be loaded in a storage device of a computer, wherein the steps of a method of at least one embodiment can be carried out with the computer program when the computer program is run on the computer.

In at least one embodiment, the invention also relates to a computer-readable medium, on which a computer program is stored, wherein the computer program can be loaded into a storage device of a computer, wherein the steps of a method of at least one embodiment can be carried out with the computer program when the computer program is run on the computer.

BRIEF DESCRIPTION OF THE DRAWINGS

The invention will be described once again in more detail below with reference to the accompanying figures and the example embodiments. The presentation in the figures is schematic and highly simplified as well as not necessarily to scale. In the drawings:

FIG. 5 shows a first illustration of an image value diagram having a base material set, FIG. 6 shows a second illustration of an image value graph having a base material set.

DETAILED DESCRIPTION OF THE EXAMPLE EMBODIMENTS

Figure 1:
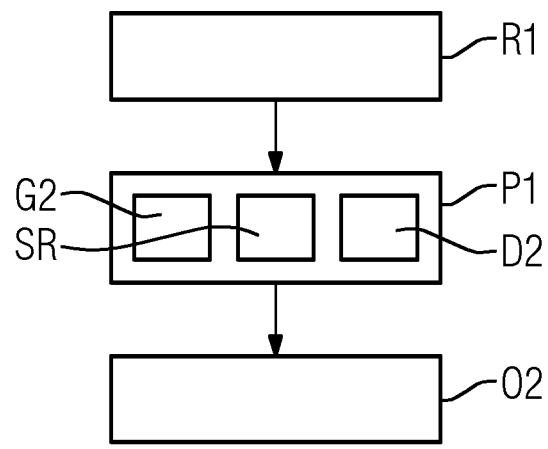
FIG. 1 shows a flowchart for a method according to a first embodiment of the invention.

At least one embodiment of the invention generally relates to a method for processing a first image data set which has been generated on the basis of multi-spectral computerized tomography imaging and which has a first image value tuple which is associated with a volume element of a region of an object to be imaged, wherein the method the comprises:

acquiring the first image data set,
processing the first image data set, and
supplying the second image data set.

Processing the first image data set, in at least one embodiment, comprises, in particular, the following steps:

wherein on the basis of the first image data set a second image data set is generated which has a second image value tuple associated with the volume element, wherein a base material decomposition can be carried on the basis of the second image data set and on the basis of a base material set, wherein a starting area and a target area are selected as a function of the base material set in the space of the image value, wherein the first image value tuple is located in the starting area, wherein the second image value tuple is ascertained on the basis of the first image value tuple, wherein the second image value tuple is associated with the first image value tuple via image value tuple mapping, and wherein the second image value tuple is located in the target area.

The first image value tuple can relate, in particular, to material which is not present in the base material set. In particular, the first image value tuple can be located in a non-physical region of the base material decomposition.

In particular, the concentration of a base material, whose concentration in the starting area is negative, in particular for image value tuples of the starting area, can be zero or be extremely low in the target area, in particular for image value tuples of the target area. The target area can be located, in particular, in a hypersurface of the space of the image values. The target area can be located, in particular, in a hypersurface of a space comprising the first image value tuple and/or the second image value tuple.

The first image value tuple can, in particular, be projected onto the hypersurface via image value tuple mapping. The second image value tuple can, in particular, be the projection of the first image value tuple onto the hypersurface.

The base material set can comprise, in particular, calcium as the base material. Calcium can be present, in particular in the form of atherosclerotic plaques, in the region to be mapped. The base material set can comprise, in particular, iodine as the base material. Iodine can be present, in particular in the form of contrast medium, in the region to be mapped. The base material set can comprise, in particular, blood and/or soft tissue as the base material. Without limiting the general inventive idea, iodine is mentioned by way of example in some of the embodiments as a contrast medium. A different contrast medium can also be used as an alternative or in addition to iodine.

In particular, a negative concentration of the base material calcium can correspond to the first image value tuple and/or a concentration of the base material calcium can correspond to the second image value tuple, which concentration is zero or is extremely low.

In particular, a positive concentration of the base material iodine can correspond to the first image value tuple and/or a non-positive concentration of the base material iodine can correspond to the second image value tuple. A non-positive concentration can, in particular, be a negative concentration.

In particular, the first image value tuple can be associated with a volume element comprising fat and/or air.

A decomposition image data set can be generated, in particular, by way of the base material decomposition on the basis of the second image data set and preferably on the basis of the base material set.

For example, the decomposition image data set can be generated by way of the base material decomposition and a noise reduction method on the basis of the second image data set and preferably on the basis of the base material set.

The noise reduction method can, in particular, be combined with the base material decomposition. The noise reduction method can be based, for example, on an iterative noise removal method and/or on a noise reduction filter, which can, in particular, be non-linear.

The decomposition image data set can, in particular, be supplied. Alternatively or additionally the decomposition image data set can be rescaled via a transformation, which can, in particular, be linear, and the rescaled decomposition image data set can be supplied. The decomposition image data set can, in particular, relate to the first base material and/or the second base material.

In particular, a first effective image value can be associated, in particular is associated, with the first image value tuple via a function. The second image value tuple can be ascertained, in particular, on the basis of the first effective image value.

In particular, a second effective image value can be associated, in particular is associated, with the second image value tuple via the function. The second effective image value can, in particular, be equal to or essentially equal to the first effective image value. The function can, in particular, be linear.

At least one embodiment of the invention also relates to an image data processing device for processing a first image data set, which has been generated on the basis of multi-spectral computerized tomography imaging and which has a first image value tuple which is associated with a volume element of a region of an object to be imaged.

In at least one embodiment, the image data processing device includes:
an acquisition module which is designed for acquiring the first image data set,
a processing module which is designed for processing the first image data set, and
a supply module, which is designed for supplying the second image data set.

In at least one embodiment, the processing module includes, in particular:
a generating module which is designed for generating a second image data set on the basis of the first image data set, wherein the second image data set has a second image value tuple associated with the volume element, wherein a base material decomposition can be carried out on the basis of the second image data set and on the basis of a base material set,
a selection module which is designed for selecting a starting area and a target area dependent on the base material set, wherein the first image value tuple is located in the starting area and outside of the target area,
an ascertaining module which is designed for ascertaining the second image value tuple on the basis of the first image value tuple, wherein the second image value tuple is associated with the first image value tuple via image value tuple mapping, wherein the second image value tuple is located in the target area.

The image data processing device can, in particular, be designed for carrying out a method of at least one embodiment.

At least one embodiment of the invention also relates to an imaging device, having an image data processing device of at least one embodiment.

In at least one embodiment, the invention also relates to a computer program product, comprising a computer program, wherein the computer program can be loaded in a storage device of a computer, wherein the steps of a method of at least one embodiment can be carried out with the computer program when the computer program is run on the computer.

In at least one embodiment, the invention also relates to a computer-readable medium, on which a computer program is stored, wherein the computer program can be loaded into a storage device of a computer, wherein the steps of a method of at least one embodiment can be carried out with the computer program when the computer program is run on the computer.

In particular, a base material decomposition can be carried out, wherein the attenuation value x of an image point of a CT image data set is interpreted as the sum of m concentrations ci of base material of a base material set with associated changes in the attenuation value per concentration yi according to:

$$x = y_0 + \sum_{i=1}^{m} y_i c_i.$$

In particular, at least m CT images $I_j$ of the same object can be recorded with different spectra in order to determine the concentrations $c_i$ at least in parts of the CT images.

In particular when there is at least one material provided in the CT image which is not incorporated by the base material set and the consequence is a negative concentration ci for at least one base material, i.e., in other words, is located in the non-physical region of the base material decomposition, the result of base material decomposition cannot be satisfactory.

To avoid an undesirable presentation of a material of this kind in at least one of the base material images, a correction can, in particular, be carried out before implementation of base material decomposition and methods of noise reduction possibly connected therewith.

The inventors have recognized that the quality of an image, which is generated on the basis of the base material decomposition, can be improved by carrying out a correction of the original image value tuples, in particular the CT values before implementation of the base material decomposition.

This correction can be implemented, in particular, by multi-dimensional imaging which suitably maps attenuation values of voxels, which would be located in the non-physical region of the base material decomposition, on other attenuation values. Improved presentation, in particular owing to better distinguishability of materials, in at least one base material image or images derived therefrom can be achieved in this way.

The materials, which are located in the non-physical region of the base material decomposition, are shifted in relation to the graph of CT values such that they are located at the desired position in the graph after implementation of the base material decomposition. For this purpose two-dimensional mapping, for example, is defined which maps a starting area onto a target area. The starting area is located in the non-physical region of the base material decomposition.

In particular, the starting area can be defined. For example, the starting area can be formed by all voxels whose image value tuples correspond to a negative calcium concentration according to base material decomposition.

In particular, it can be defined how these voxels should be presented after base material decomposition. For example, the voxels in the blood/iodine image can be presented with the original CT value, which would be associated with the voxel in a linearly weighted mixed image, which can be generated on the basis of the first image data set. In particular, the conditions, for example the relevant equations, for image value tuple mapping can be determined.

For example, after the shift in the graph the voxel can have the same CT value in the mixed image as before the shift, and this corresponds to a first equation. For example, after the shift the voxel can be located in the graph on the straight line, which corresponds to a calcium concentration of zero, and this corresponds to a second equation.

Image value tuple mapping can be ascertained, in particular on the basis of the conditions, in particular the mapping equations, for the image value tuple mapping.

For example, linear mapping, which is a function of the CT values in the two original images, can be ascertained by solving the equation system, which comprises the first equation and the second equation.

This method can also be used for multi-energy scanners having more than two spectra, in particular having more than two energies. In particular, straight lines can be replaced by surfaces or hyperplanes.

The method can accordingly also be applied on the basis of mono-energy images, as are generated by some dual-/multi-energy CT scanners. The method can also be applied if a base material decomposition has already taken place with a different physically expedient region and is to be changed to a different material base. In this case the method can also use the base material images, in particular of a decomposition image data set, as the starting point. The image values of an image value tuple in a base material image can be given, for example, in Hounsfield units or relate to a material density in mg/ml.

With the aid of the correction, which is made before base material decomposition (and optional noise reduction), image artifacts, which are caused by image value tuples which are located in and/or at the edge of the non-physical region of base material decomposition, can be avoided in the obtained base material images.

At least one embodiment therefore enables, in particular, an improvement in a base material decomposition on the basis of a multi-energy CT image data set.

At least one embodiment enables, in particular, an improvement in the image quality of base material images, for example much better separation of vessels and fatty tissue. In particular, image value tuples of fat and/or air are mapped such that they are interpreted as negative or extremely low concentrations of iodine during base material decomposition.

In particular because the correction can be made on the basis of mapping of CT values onto other CT values, no assumptions have to be made as to which materials are present outside of the physically expedient region of the base material decomposition.

At least one embodiment also enables a subtraction of vascular calcification by at least approximately correct consideration of partial volume effects, and can thereby be used as the basis for new clinical application of dual-energy computerized tomography.

The first image data set can be, for example, a medical first image data set and/or relate to a region of an object to be imaged. The second image data set can be, for example, a medical second image data set and/or relate to the region of the object to be imaged. The object can be, for example, a patient. The first image data set can be reconstructed, for example, from an imaging raw data set. The imaging raw data set can be acquired, for example, via an imaging device. The first image data set can be acquired, for example, via a medical imaging device. The first image data set can represent, for example, anatomical structures and/or functional processes of a region of an object to be imaged.

The first image data set can be, for example, a multi-energy computerized tomography image data set, in particular a dual-energy computerized tomography image data set.

The imaging device can acquire, for example, a first imaging raw data set with a first radiation which has a first spectrum and/or a first characteristic energy. The imaging device can acquire, for example, a second imaging raw data set with a second radiation which has a second spectrum and/or a second characteristic energy. The first image data set can be reconstructed, for example, on the basis of the first imaging raw data set and on the basis of the second imaging raw data set via the imaging device. The imaging device can be, for example, a dual-energy computer tomograph and/or a multi-energy computer tomograph. The imaging device can be, for example, a dual-source computer tomograph and/or a multi-source computer tomograph. The imaging device can have, for example, a plurality of different filters for filtering the radiation.

The first image data set can have, for example, an image point. The image point can have, for example, an item of position information and an image value tuple. The position information can relate, for example, to the position of a volume element of a region of an object to be imaged.

Acquiring the first image data set can comprise an acquisition of the first image data set via an imaging device. Alternatively, acquiring the first image data set can comprise loading the first image data set from an image database.

The first image data set can be processed, in particular, via an algorithm, which is run on a computer. The algorithm can comprise, for example, the first image data set as the input parameter. The algorithm can comprise, for example, the second image data set as the output value.

Supplying the second image data set can comprise outputting the second image data set for a user via an output device and/or storing the second image data set in a database.

The decomposition image data set can, in particular, be and/or comprise a base material image. In particular, a value of an image point of the decomposition image data set can be ascertained on the basis of the second image value tuple.

Supplying the decomposition image data set can comprise displaying the decomposition image data set for a user via an output device and/or storing the decomposition image data set in a database.

An image value tuple can be associated, for example, with a volume element of a region of an object to be imaged. An image value tuple can have a plurality of image values. An image value can be and/or represent, for example, an attenuation value, a computerized tomography value, an intensity value, a Hounsfield value, a gray-scale value, a concentration, a density or the like.

The image value tuple can be presented, in particular, in relation to a base component set. The base component set can be, in particular, a base material set and/or have a base material set. The base component set can have a plurality of base components. In particular, the base material set can have a first base material and/or a second base material. For example, an image value of the image value tuples can be associated with each base component of the base component set. In particular the image value can be taken to mean a measure of the presence and/or the relevance of the base component, with which the image value is associated, in the volume element with which the image value tuple is associated.

A base component can be, for example, a base material, a basic energy, a basic spectrum, a basic parameter or combinations thereof.

A base material can be, for example, a contrast medium, in particular iodine, tissue, in particular soft tissue, blood, water, bone, cartilage, fat and the like. A base material can be, for example, a combination and/or a mixed form comprising a plurality of materials. Additional assumptions, in particular boundary conditions, in relation to the density of the plurality of materials can also be considered. An image value, which is associated with a base material, can correspond, for example, to a concentration, a volume fraction, a mass fraction or a density of the base material.

A base component set can have, for example, a contrast medium, in particular iodine, as a first base component and a mixed form comprising blood and bone as the second base component. Accordingly, the image value tuple can have a contrast medium concentration as the first image value and a concentration of the mixed form as the second image value. The concentration of the mixed form, which will also be called the mixed form concentration below, can be defined, for example, in such a way that with a first mixed form concentration, the concentration of a first material of the mixed form is zero and that with a second mixed form concentration, the concentration of a second material of the mixed form is zero. Instead of the mixed form concentration the concentration of a material of the mixed form can also be used, with a given concentration of the other material of the mixed form being taken into account as a constant contribution. Details relating to the base materials are known to a person skilled in the art in particular in the context of two-material decomposition and three-material decomposition.

A basic energy can be, for example, the energy of a radiation with which the image value was recorded. A basic spectrum can be, for example, the spectrum of a radiation with which the image value was recorded.

An image value which is associated a with basic energy and/or a basic spectrum can be, for example, an attenuation value, a computerized tomography value, an intensity value or the like. Different basic energies and/or different basic spectra can be achieved in computerized tomography, for example by different radiation sources, different tube voltages and/or different filters. Details relating to basic energies or basic spectra are known to a person skilled in the art in particular in the context of dual- or multi-energy computerized tomography, dual- or multi-source computerized tomography, dual- or multi-spectra computerized tomography.

Multi-spectral computerized tomography can, in particular, be taken to mean multi-energy computerized tomography, in particular dual-energy-computerized tomography, multi-source computerized tomography, in particular multi-source computerized tomography, multi-spectra computerized tomography, in particular multi-source computerized tomography, or the like or a combination thereof.

A basic parameter can relate, for example, to a type of interaction, for example via a photoelectric effect and/or via Compton scattering, of radiation with an object. A basic parameter can be, for example, a suitable combination of an electron density, an atomic number, a mass number and/or further, physical and/or chemical parameters relating to the volume element. A base component set can have, for example, a first basic parameter, which relates to the photoelectric effect, as the first base component and a second basic parameter, which relates to Compton scattering, as the second basic component. Accordingly, the first image value can be an attenuation value which is a measure of the relevance of the photoelectric effect in the volume element, and the second image value can be an attenuation value, which is a measure of the relevance of Compton scattering in the volume element. Details relating to basic parameters are known to a person skilled in the art in particular from [AM76].

A base component set for a presentation of the image value tuples can be selected from a large number of possible base component sets. In different base component sets the image values of the image value tuples can be different and/or have different meanings. A choice and/or transformation can be made between the presentations of the image value tuples in different base component sets without departing from the scope of the invention which is specified by the claims.

The first image value tuple can be located, for example, in a starting area. The starting area can be selected, for example, as a function of a base material set. The embodiments described in connection with the target area, which relate to the selection of the target area, can, for example, be transferred accordingly to the starting area. The starting area can have, for example, one or more start image value tuple(s). The starting area can be, for example, non-physical in relation to the base material set and/or in relation to base material decomposition. In particular, a concentration of a base material of the base material set, which corresponds to the start image value tuple, can be negative for each start image value tuple of the starting area. The first image value tuple is then located in the starting area, in particular, when it is located in the starting area in relation to a base component system in which the starting area is presented.

The target area can have one or more target image value tuple(s). The statements described here relating to the image value tuple apply accordingly to each target image value tuple. In particular, the target image value tuples of the target area can have different target image values depending on the base component system which has been selected for the presentation of the target area. The target area can be selected, for example, in relation to a base component system in which the first image value tuple and/or the second image value tuple is/are presented.

The hypersurface, in which the target area is located, can be, for example, a hyperplane, a surface, a plane, a curve or a straight line. The hypersurface can be defined, for example, in that the concentration of a given base material of the base material set, for example calcium, corresponding to the image value tuple, is equal to a given concentration for all image value tuples which are located in the hypersurface. The given concentration can be, for example, zero or an extremely low value.

In particular, the first image data set can have a plurality of first image value tuples. In particular, the second image data set can have a plurality of second image value tuples. In particular, the second image data set for each first image value tuple of the plurality of first image value tuples can have a second image value tuple of the plurality of second image value tuples, which is associated with the same volume element as the respective first image value tuple of the plurality of first image value tuples and which is ascertained on the basis of the respective first image value tuple of the plurality of first image value tuples.

According to one embodiment of the invention it can be provided that the starting area comprises the plurality of first image value tuples and/or that the target area comprises the plurality of second image value tuples and/or that for each first image value tuple of the plurality of first image value tuples a second image value tuple of the plurality of second image value tuples is ascertained, which is associated with the respective first image value tuple via image value tuple mapping. In particular, the starting area and the target area can overlap or be disjunct.

According to a further embodiment of the invention it can be provided that different starting areas and/or different image value tuple mappings are used for the first image value tuples of the plurality of first image value tuples and/or that different target areas are used for the second image value tuples of the plurality of second image value tuples. For example, a target area relating to a first image value tuple, which relates to a first volume element, and a starting area relating to a first image value tuple, which relates to a second volume element, can overlap and/or be identical. For example, the first image value tuple can be located in the starting area, in particular of the first image value tuple, and/or outside of the target area, in particular of the first image value tuple.

Furthermore, in particular it is not necessary for a respective image value tuple to be ascertained in the target area for all image value tuples of the first image data set, which are located in the non-physical region. The first image value tuple and/or the plurality of first image value tuples, for example, can be selected on the basis of at least one selection criterion from the image value tuples of the first image data set which is located in the non-physical region.

The first image value tuple can, in particular, be located outside of the target area when a projection of the first image value tuples onto the hypersurface is located outside of the target area.

The first image value tuple is located outside of the target area, in particular, when it is located outside of the target area in relation to a base component system in which the target area is presented. The second image value tuple is located outside of the target area, in particular, when it is located outside of the target area in relation to a base component system in which the target area is presented. The second image value tuple is located in the target area, in particular, when it is located in relation to a base component system, in which the target area is presented, in the target area.

The target area can be selected, for example, fully automatically, automatically, semi-automatically or manually. The target area can, in particular, be selected in such a way that the or the plurality of target image value tuple(s) of the target area and/or the second image value tuple can be presented in an improved manner, in the case of a base material decomposition based on the base material set, compared to the first image value tuple, in particular can be distinguished better from an image value tuple that relates to a base material of the base material set. The target area can, in particular, be selected in such a way that the material, which is not provided in the base material set, can be distinguished better in the decomposition image data set from the first and/or the second base material(s).

The target area is selected as a function of a base material set, in particular, when the target area is selected as a function of one or more base material(s) of the base material set.

The target area is selected as a function of a base material set, in particular, when the target area is selected as a function of a concentration of a base material of the base material set or as a function of a plurality of concentrations which are each associated with one of the base materials of the base material set. The target area can be selected, for example, as a function of a base material set by selecting a concentration of a base material of the base material set or a plurality of concentrations which are each associated with one of the base materials of the base material set.

The target area can be selected in such a way, for example, that for all image value tuples of the target area the concentration corresponding to the image value tuple in each case is equal to the selected concentration, or the concentrations corresponding to the image value tuple in each case are equal to the selected concentrations.

Concentration of a base material can, for example, also be taken to mean a density, a mass fraction, a volume fraction, a coefficient of the base material or the like.

In particular, a concentration of a base material of the base material set, which corresponds to the image value tuple, can be negative for each image value tuple of the non-physical region. The second image value tuple can be ascertained, for example, on the basis of the target area. The second image value tuple can be ascertained in such a way, for example, that it is located in the target area.

A first concentration of the first base material and/or a second concentration of the second base material can, in particular, correspond to the first image value tuple.

A first concentration of the first base material corresponds to the first image value tuple, in particular, when the first image value tuple presented in relation to the base material set has the first concentration of the first base material as an image value.

A second concentration of the second base material corresponds to the first image value tuple, in particular, when the first image value tuple presented in relation to the base material set has the second concentration of the second base material as an image value.

A third concentration of the first base material and/or a fourth concentration of the second base material can correspond, in particular, to the second image value tuple.

A third concentration of the third base material corresponds to the second image value tuple, in particular, when the second image value tuple presented in relation to the base material set has the third concentration of the third base material as an image value.

A fourth concentration of the fourth base material corresponds to the second image value tuple, in particular, when the second image value tuple presented in relation to the base material set has the fourth concentration of the fourth base material as an image value.

The first concentration can, in particular, be different to the third concentration. The second concentration can, in particular, be different to the fourth concentration.

In particular, a sign of the first concentration can be different to a sign of the third concentration. In particular, a sign of the second concentration can be different to a sign of the fourth concentration. In particular, the first concentration can be positive and/or the third concentration can be negative. In particular, the second concentration can be negative and/or the fourth concentration can be zero or be extremely low.

For example, a first threshold value concentration can be selected in such a way that the first threshold value concentration is less than the first concentration and greater than the third concentration or that the first threshold value concentration is greater than the first concentration and less than the third concentration.

For example, a second threshold value concentration can be selected in such a way that the second threshold value concentration is less than the second concentration and greater than the fourth concentration or that the second threshold value concentration is greater than the second concentration and is less than the fourth concentration.

The target area can be selected, for example, as a function of a base material set by selecting the first threshold value concentration and/or by selecting the second threshold value concentration. The target area can be limited, for example, by the first threshold value concentration and/or by the second threshold value concentration.

Image value tuple mapping can be, for example, mapping of the starting area into the target area. In particular, image value tuples of the target area can be associated with image value tuples of the starting area via image value tuple mapping. The second image value tuple can be ascertained, for example, on the basis of image value tuple mapping, with a second image value tuple being associated with the first image value tuple via image value tuple mapping. Image value tuple mapping can be, for example, linear and/or multi-dimensional.

The function, with which a first effective image value can be associated with the first image value tuple and/or with which a second effective image value can be associated with the second image value tuple can be, for example, linear mapping, in particular a linear combination, and/or a mean of the image values of the image value tuples which is used as an argument for the function.

The first effective image value can be, for example, a first effective attenuation value, a sum of the image values of the first image value tuple and/or a weighted mean of the image values of the first image value tuple. The second effective image value can be, for example, a second effective attenuation value, a sum of the image values of the second image value tuple and/or a weighted mean of the image values of the second image value tuple.

Image value tuple mapping can be ascertained and/or selected, for example, on the basis of the first effective image value. In particular, image value tuple mapping can be ascertained and/or selected in such a way that the first effective image value is equal to the second effective image value.

A method for processing a first image data set, which has a first image value tuple, can, in particular, comprise:
  acquiring the first image data set,
  processing the first image data set,
  wherein on the basis of the first image data set a second image data set is generated which has a second image value tuple,
  wherein a target area is selected as a function of a base material set,
  wherein the first image value tuple is located outside of the target area,
  wherein the second image value tuple is ascertained on the basis of the first image value tuple,
  wherein the second image value tuple is located in the target area,
  supplying the second image data set.

An image data processing device for processing a first image data set, which has a first image value tuple, can include:
  an acquisition module which is designed for acquiring the first image data set,
  a processing module which is designed for processing the first image data set, having
  a generating module which is designed for generating a second image data set on the basis of the first image data set, wherein the second image data set has a second image value tuple,
  a selection module which is designed for selecting a target area as a function of the base material set, wherein the first image value tuple is located outside of the target area,
  an ascertaining module which is designed for ascertaining the second image value tuple on the basis of the first image value tuple, wherein the second image value tuple is located in the target area,
  a supply module which is designed for supplying the second image data set.

According to one embodiment of the invention the imaging device is a medical imaging device. According to one embodiment of the invention the imaging device is selected from the group comprising a C-arm X-ray machine, a computer tomograph (CT device), a single photon emission computer tomograph (SPECT device), a positron emission tomograph (PET device), a magnetic resonance tomograph (MRT system) and combinations thereof. In particular, the imaging device can have an X-ray machine, an ultrasound scanner or the like. The imaging device can also be a combination of a plurality of imaging and/or irradiation modalities. An irradiation modality can have, for example, an irradiation unit for therapeutic irradiation.

According to one embodiment of the invention the first image data set is generated and/or supplied via the imaging device. According to one embodiment of the invention the imaging device is designed to generate and/or supply the first image data set.

One embodiment of the invention provides that the inventive image data processing device and/or one or more components of the inventive image data processing device are implemented on a processor system at least partially in the form of software. In particular the acquisition module, processing module, supply module, generating module, selection module and ascertaining module can each form one component of the inventive image data processing device. One embodiment of the invention provides that the inventive image data processing device and/or one or more components of the inventive image data processing device are implemented at least partially in the form of software-assisted hardware, for example FPGAs, a processor system or the like.

Data can be transferred between components of the image data processing device, for example, via a suitable interface. One embodiment of the invention provides that interfaces for data transfer to and/or from components of the inventive image data processing device are implemented at least partially in the form of software. In particular, the interfaces can have access to suitable storage areas in which data can be appropriately buffered, retrieved and updated. The interfaces can also be designed as hardware interfaces which are controlled by the appropriate software.

An implementation of an embodiment of the inventive image data processing device largely in terms of software has the advantage that even previously used imaging devices and/or computers can be upgraded by way of a software update in order to work inventively. In this respect the object is also achieved by a corresponding computer program product having a computer program which can be loaded into a storage device of a computer, wherein the steps of an embodiment of the inventive method can be carried out with the computer program when the computer program is run on the computer. Aside from the computer program a computer program product of this kind can comprise additional software components, e.g. documentation, and/or hardware components, e.g. a hardware key (dongle, etc.) in order to use the software.

For transporting the computer program and/or storing the computer program on or in a computer, a computer-readable medium, for example a memory stick, a hard disk or another transportable or permanently installed data carrier can be used on which a computer program is stored which can be loaded into a storage device of a computer, wherein the steps of an embodiment of an inventive method can be carried out with the computer program when the computer program is run on the computer. One embodiment of the invention provides that the inventive imaging device and/or the inventive image data processing device has/have a computer. The computer can have a processor system in each case, and this has, for example, a microprocessor or a plurality of collaborating microprocessors.

Within the context of the invention features which are described in relation to different embodiments and/or different categories of claims (method, image data processing device, etc.), can be combined to form further embodiments. In particular features, advantages and embodiments described in relation to the inventive method can also be transferred to the inventive image data processing device, the inventive computer program product and the inventive computer-readable medium and vice versa. In other words, the concrete claims can also be developed with the features which are described or claimed in conjunction with a method. Functional features of an inventive method can be implemented by appropriately designed components or modules of the inventive image data processing device.

The described method and described image data processing device are only embodiments of the invention. The invention can be varied by a person skilled in the art without the departing from the scope of the invention insofar as it is specified by the claims.

The use of the indefinite article "a" or "an" does not prevent the relevant features from also being present multiple times. The use of the expression "has/have" does not preclude the terms linked by way of the term "has/have" from being identical. For example, the medical imaging device has the medical imaging device. It is possible for a module to have a plurality of spatially separate sub-modules.

The use of ordinal numbers (first, second, third, etc.) in the identification of features is primarily used in the context of the present application in order to be able to distinguish the features identified by the use of ordinal numbers better. The absence of a feature, which is identified by a combination of a given ordinal number and a term, does not preclude a feature from being present which is identified by a combination of an ordinal number, which follows the given ordinal number, and the term.

Within the context of the present application the expression "on the basis of" can, in particular, be interpreted within the meaning of the expression "using". In particular, wording according to which a first feature is generated (alternatively: ascertained, determined, etc.) on the basis of a second feature, does not preclude the first feature from being generated (alternatively: ascertained, determined, etc.) on the basis of a third feature.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

FIG. 1 shows a flowchart for a method for processing a first image data set according to a first embodiment of the invention. The first image data set has been generated on the basis of multi-spectral computerized tomography imaging and has a first image value tuple X which is associated with a volume element of a region of an object to be mapped. The object can, in particular, be the patient 13.

The first image data set is acquired in step R1. The first image data set is processed in step P1. The second image data set is supplied in step O2.

A second image data set is generated in step G2 on the basis of the first image data set, which second set has a second image value tuple Y associated with the volume element. A starting area and a target area are selected as a function of a base material set in step SR, with the first image value tuple being located in the starting area. The second image value tuple is ascertained on the basis of the first image value tuple in step D2, with the second image value tuple being located in the target area.

Figure 2:
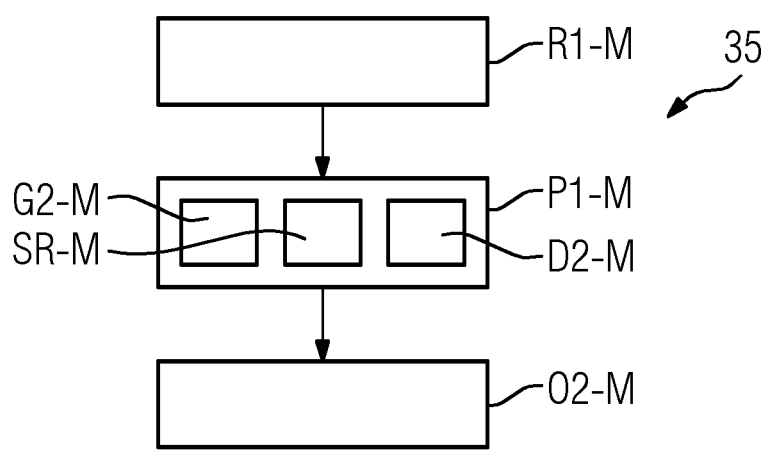
FIG. 2 shows a schematic illustration of an image data processing device according to a second embodiment of the invention.

FIG. 2 shows a schematic illustration of an image data processing device 35 according to a second embodiment of the invention, having an acquisition module R1-M, a processing module P1-M, a generating module G2-M, a selection module SR-M, an ascertaining module D2-M and a supply module O2-M.

Figure 3:
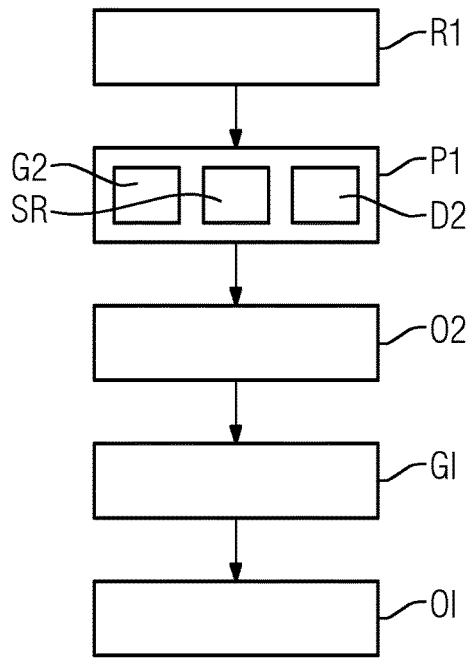
FIG. 3 shows a flowchart for a method according to a third embodiment of the invention.

FIG. 3 shows a flowchart for a method for processing a first image data set according to a third embodiment of the invention. A decomposition image data set is generated in step GI on the basis of the second image data set and on the basis of the base material set by way of a base material decomposition. The decomposition image data set is supplied in step OI.

Figure 4:
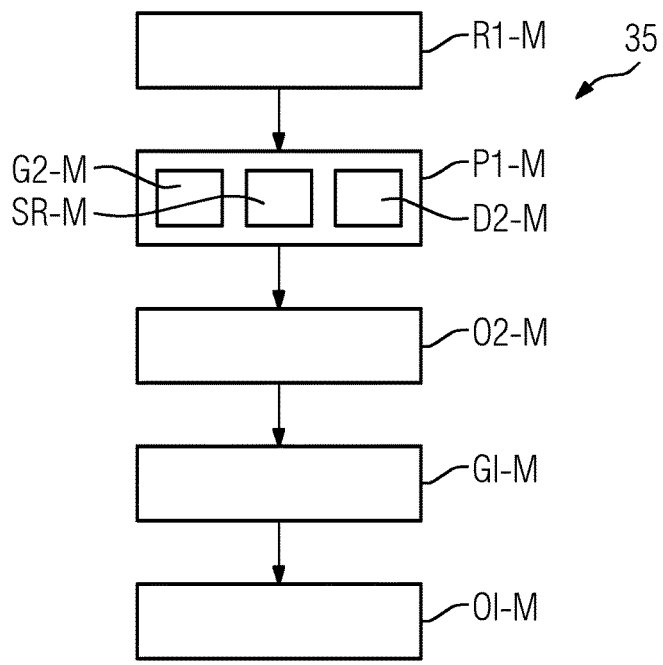
FIG. 4 shows a schematic illustration of an image data processing device according to a fourth embodiment of the invention.

FIG. 4 shows a schematic illustration of an image data processing device 35 according to a fourth embodiment of the invention, having a base material decomposition module GI-M and a decomposition image data set supply module OI-M.

The base material decomposition module GI-M is designed for generating a decomposition image data set on the basis of the second image data set and on the basis of the base material set by way of a base material decomposition. The decomposition image data set supply module OI-M is designed for supplying the decomposition image data set.

FIG. 5 and FIG. 6 each show an illustration of an image value graph, having a base material set with the base materials blood P0, calcium P2 and iodine PI.

The axis M1 relates to the concentration of the base material iodine. The axis M2 relates to the concentration of a mixed form comprising the base material blood (or soft tissue) and calcium. The concentration of the base material calcium is zero at the points which lie on the axis M1. The concentration of the base material iodine is zero at the points which lie on the axis M2. In particular, the calcium concentration is zero at point P0.

The axis E1 relates to computerized tomography values in the case of a first characteristic energy of a first radiation. The axis E2 relates to computerized tomography values in the case of a second characteristic energy of a second radiation. The second characteristic energy can, for example, be higher than the first characteristic energy. The first image value tuple X can, in particular, be presented in relation to the basic energies E1 and E2 having the image values XE1 and XE2.

The first image value tuple X relates to the material fat which is not present in the base material set. The first image value tuple X can, in particular, be presented in relation to the base material set having the image values XM1 and XM2. The iodine concentration is positive at point XM1. The calcium concentration is negative at point XM2.

The region RI is physical in relation to the base material set. The region R2 is non-physical in relation to the base material set. In particular, can the starting area can be located in the region R2. In particular, the target area can comprise a semi-axis of the axis M1 which corresponds to negative concentrations of the base material iodine.

The target area can optionally comprise a region of the axis M1, corresponding to positive concentrations of the base material iodine, with the concentrations being less than a threshold value concentration of the base material iodine. This threshold value concentration can be selected in such a way, for example, that an iodine concentration, which is greater than the threshold value concentration, is associated with a volume element in which at least a given quantity of iodine, for example a diagnostically relevant quantity of iodine, is present.

In particular, the threshold value concentration of the base material iodine can be less than or equal to a fraction, for example half or a tenth or a fiftieth, of the maximum value for the concentration of the base material iodine in the first image data set.

In particular, an extremely low concentration of a base material can be taken to mean a concentration of the base material which is less than or equal to a fraction, for example half or a tenth or a fiftieth, of the maximum value for the concentration of the base material in the first image data set.

In particular, an extremely low concentration of the base material iodine can be taken to mean a concentration of the base material iodine which is less than or equal to a fraction, for example half or a tenth or a fiftieth, of the maximum value for the concentration of the base material iodine in the first image data set.

In particular, an extremely low concentration of the base material calcium can be taken to mean a concentration of the base material calcium which is less than or equal to a fraction, for example half or a tenth or a fiftieth, of the maximum value for the concentration of the base material calcium in the first image data set.

The second image value tuple Y is ascertained on the basis of image value tuple mapping A1 and on the basis of the first image value tuple X. Possible image value tuple mappings are symbolized by the arrows A2. A negative iodine concentration corresponds to the second image value tuple Y. A calcium concentration corresponds to the second image value tuple Y, and this is zero or extremely low. The second image value tuple Y can be presented, in particular, in relation to the basic energies E1 and E2 having the image values YE1 and YE2.

According to one embodiment of the invention the first image value tuple X can be mapped onto the second image value tuple Y in such a way that the spacing of the second image value tuple Y from the axis M1 is less than or equal to a fraction, for example a tenth, of the spacing of the first image value tuples X from the axis M1.

Figure 7:
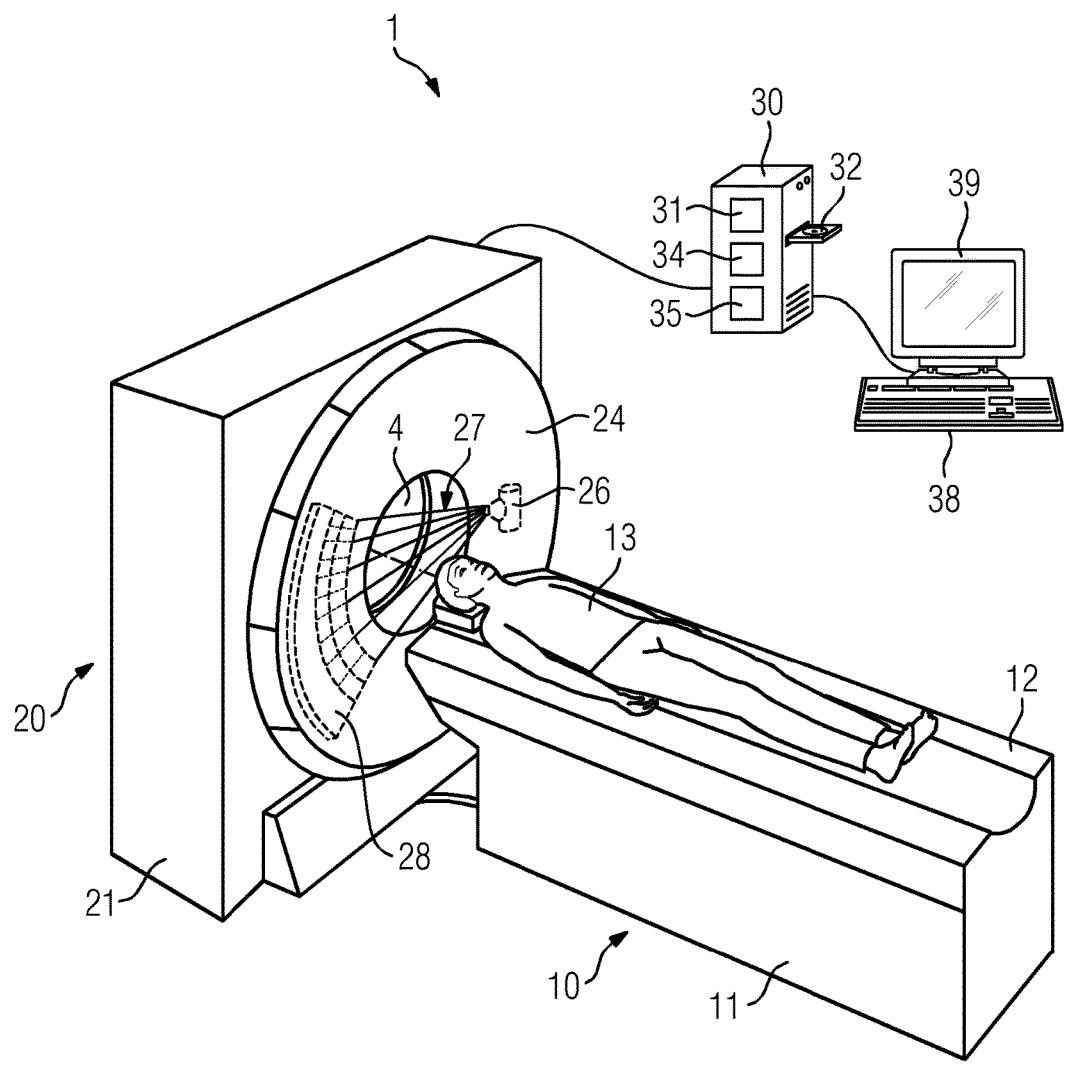
FIG. 7 shows a schematic illustration of an imaging device according to a fifth embodiment of the invention.

FIG. 7 shows a schematic illustration of an imaging device 1 according to a fifth embodiment of the invention, having an acquisition region 4 formed by a tunnel-shaped opening, wherein the patient positioning device 10 has a patient table 11, wherein the tabletop 12 is arranged on the patient table so it can be moved relative to the patient table 11 in such a way that the tabletop 12 can be introduced into the acquisition region 4 in a longitudinal direction of the tabletop 12. A computer tomograph 1 is shown by way of example of an imaging device 1 without limiting the general inventive idea.

The imaging device 1 has a gantry 20, the acquisition region 4, the patient positioning device 10, an imaging raw data acquisition device 26, 28 and a controller 30. The gantry 20 has a stationary support frame 21 and a rotor 24. The rotor 24 is mounted by way of a pivot bearing device so it can rotate about an axis of rotation. The acquisition region 4 is formed by a tunnel-shaped opening in the gantry 20. A region of an object, in particular of the patient 13, to be mapped can be arranged in the acquisition region 4.

The imaging raw data acquisition device 26, 28 is a projection data acquisition device 26, 28 having a radiation source 26, e.g. an X-ray source, and a detector 28, e.g. an X-ray detector. The radiation source 26 is arranged on the rotor 24 and designed for emission of radiation, e.g. X-ray radiation, having radiation quanta 27. The detector 28 is arranged on the rotor 24 and designed for detection of the radiation quanta 27. The radiation quanta 27 can pass from the radiation source 26 to the region to be mapped and, following an interaction with the region to be mapped, strike the detector 28. Projection data of the region to be mapped can be acquired in this way. The projection data acquired by the projection data acquisition device 26, 28 is forwarded to the controller 30. The controller 30 is a computer, in particular a digital computer, and designed for controlling the imaging device 1. The controller 30 has the processor system 31 and the computer-readable medium 32. The controller 30 has an image reconstruction device 34 and the image processing device 35. An image can be reconstructed via the image reconstruction device 34 on the basis of the projection data.

The imaging device 1 has an input device 38 and an output device 39. The input device 38 is designed for inputting control information, e.g. image reconstruction parameters and/or examination parameters. The output device 39 is designed for outputting control information and/or images.

The imaging device 1 according to the fifth embodiment of the invention has the inventive image data processing device 35.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for processing a first image data set, generated on the basis of multi-spectral computerized tomography imaging and including a first image value tuple associated with a volume element of a region of an object to be imaged, the method comprising:
   acquiring the first image data set;
   processing the first image data set, the processing including
      generating, on the basis of the first image data set, a second image data set including a second image value tuple associated with the volume element, wherein a base material decomposition is carried out on the basis of the second image data set and on the basis of a base material set,
      selecting a starting area and a target area in the space of the image values as a function of the base material set, the first image value tuple being located in the starting area,
      ascertaining the second image value tuple on the basis of the first image value tuple, the second image value tuple being associated with the first image value tuple via image value tuple mapping and the second image value tuple being located in the target area; and supplying the second image data set.

2. The method of claim 1, wherein at least one of
   the first image value tuple relates to a material, not present in the base material set, and
   the first image value tuple is located in a non-physical region of the base material decomposition.

3. The method of claim 2, wherein at least one of a concentration of a base material for image value tuples of the target area, whose concentration is negative for image value tuples of the starting area, is zero or is extremely low and the target area is located in a hypersurface of the space of the image values.

4. The method of claim 2, wherein the base material set comprises calcium and iodine as the base material, a negative concentration of the base material calcium corresponds to the first image value tuple, and a concentration of the base material calcium, which is zero or extremely low, corresponds to the second image value tuple.

5. The method of claim 4, wherein at least one of
   a positive concentration of the base material iodine corresponds to the first image value tuple, and a concentration of the base material iodine, which is non-positive or extremely low, corresponds to the second image value tuple.

6. The method of claim 2, wherein a decomposition image data set is generated on the basis of the second image data set and on the basis of the base material set by way of the base material decomposition, and wherein the decomposition image data set is supplied.

7. The method of claim 6, wherein the decomposition image data set relates to at least one of the first base material and the second base material.

8. The method of claim 2, wherein a first effective image value is associateable with the first image value tuple via a function, and wherein the second image value tuple is ascertained on the basis of the first effective image value.

9. The method of claim 8, wherein a second effective image value is associateable with the second image value tuple via the function, and wherein the second effective image value is equal to the first effective image value.

10. The method of claim 9, wherein the function is linear.

11. The method of claim 8, wherein the function is linear.

12. The method of claim 1, wherein at least one of a concentration of a base material for image value tuples of the target area, whose concentration is negative for image value tuples of the starting area, is zero is extremely low and the target area is located in a hypersurface of the space of the image values.

13. The method of claim 1, wherein the base material set comprises calcium and iodine as the base material, a negative concentration of the base material calcium corresponds to the first image value tuple, and a concentration of the base material calcium, which is zero or extremely low, corresponds to the second image value tuple.

14. The method of claim 13, wherein at least one of
a positive concentration of the base material iodine corresponds to the first image value tuple, and
a concentration of the base material iodine, which is non-positive or extremely low, corresponds to the second image value tuple.

15. The method of claim 1, wherein a decomposition image data set is generated on the basis of the second image data set and on the basis of the base material set by way of the base material decomposition, and wherein the decomposition image data set is supplied.

16. The method of claim 15, wherein the decomposition image data set relates to at least one of the first base material and the second base material.

17. The method of claim 1, wherein a first effective image value is associateable with the first image value tuple via a function, and wherein the second image value tuple is ascertained on the basis of the first effective image value.

18. The method of claim 17, wherein a second effective image value is associateable with the second image value tuple via the function, and wherein the second effective image value is equal to the first effective image value.

19. The method of claim 18, wherein the function is linear.

20. The method of claim 17, wherein the function is linear.

21. A non-transitory memory, comprising a computer program to carry out the method of claim 1 when the computer program is run on a computer.

22. A non-transitory computer-readable medium including a computer program, the computer program being loadable into a storage device of a computer, the computer program being configured to carry out the method of claim 1 when the computer program is run on the computer.

23. An image data processing device for processing a first image data set, generated on the basis of multi-spectral computerized tomography imaging and including a first image value tuple associated with a volume element of a region of an object to be imaged, the image data processing device comprising:
an acquisition module, to acquire the first image data set;
a processing module to process the first image data set, the processing module including
a generating module to generate a second image data set on the basis of the first image data set, the second image data set including a second image value tuple associated with the volume element, wherein a base material decomposition is carried out on the basis of the second image data set and on the basis of a base material set,
a selection module to select a starting area and a target area as a function of the base material set, the first image value tuple being located in the starting area, and
an ascertaining module to ascertain the second image value tuple on the basis of the first image value tuple, the second image value tuple being associated with the first image value tuple via image value tuple mapping, and the second image value tuple being located in the target area; and
a supply module to supply the second image data set.

24. The image data processing device of claim 23, wherein at least one of
the first image value tuple relates to a material, not present in the base material set, and
the first image value tuple is located in a non-physical region of the base material decomposition.

25. An imaging device, comprising the image data processing device of claim 24.

26. An imaging device, comprising the image data processing device of claim 23.

27. An image data processing device for processing a first image data set, generated on the basis of multi-spectral computerized tomography imaging and including a first image value tuple associated with a volume element of a region of an object to be imaged, the image data processing device comprising:
a memory storing computer-readable instructions;
at least one processor configured to execute the computer-readable instructions to acquire the first image data set and to process the first image data set, the processing including
generating a second image data set on the basis of the first image data set, the second image data set including a second image value tuple associated with the volume element, wherein a base material decomposition is carried out on the basis of the second image data set and on the basis of a base material set,
selecting a starting area and a target area as a function of the base material set, the first image value tuple being located in the starting area, and
ascertaining the second image value tuple on the basis of the first image value tuple, the second image value tuple being associated with the first image value tuple via image value tuple mapping, and the second image value tuple being located in the target area; and
a supply module to supply the second image data set.

28. The image data processing device of claim 27, wherein at least one of
the first image value tuple relates to a material, not present in the base material set, and the first image value tuple is located in a non-physical region of the base material decomposition.

29. An imaging device, comprising the image data processing device of claim 28.

30. An imaging device, comprising the image data processing device of claim 27.

\* \* \* \* \*